(12) United States Patent
Sugiya et al.

(10) Patent No.: US 6,177,591 B1
(45) Date of Patent: Jan. 23, 2001

(54) OPTICALLY ACTIVE PHOSPHINE OXIDE CARBOXYLIC ACID AND METHOD OF PRODUCING THE SAME

(75) Inventors: Masashi Sugiya, Tokyo; Hiroyuki Nohira, Urawa, both of (JP)

(73) Assignee: Nippon Chemical Industrial Co., Ltd., Tokyo (JP)

( * ) Notice: Under 35 U.S.C. 154(b), the term of this patent shall be extended for 0 days.

(21) Appl. No.: 09/371,050

(22) Filed: Aug. 10, 1999

(51) Int. Cl.[7] .................................................... C07B 57/00
(52) U.S. Cl. ...................... 562/401; 562/512; 562/553; 562/579
(58) Field of Search ...................... 562/401, 512, 562/579, 553

(56) References Cited

U.S. PATENT DOCUMENTS 3,770,513 * 11/1973 Wystrach .
4,983,756 * 1/1991 Lukas et al. ..................... 562/401

OTHER PUBLICATIONS

CA:122:10116 Tetrahedron Lett by Kielbasinski 35(38) pp. 7081–7084, 1994.*
CA:103:196510 Tetrahedron Lett by Imamoto 26(6) pp. 783–786, 1985.*
Chemistry Letters by Sugiya No. 6 pp. 479–480, 1998.*
CA:82:43518 Zh Obshch Khim 44(10) pp. 2125–2129 by Aleksandrova, 1974.*

* cited by examiner

Primary Examiner—Jean F. Vollano
(74) Attorney, Agent, or Firm—Armstrong, Westerman, Hattori, McLeland & Naughton

(57) ABSTRACT

An optically active 1-phenylethylamine is reacted to a phosphine oxide carboxylic acid of a racemic modification shown by the following general formula (2):

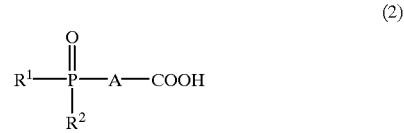

and a produced diastereomeric salt is separated using the difference in solubility against a solvent, which is subsequently decomposed by acid, so as to free and separate an optically active phosphine oxide carboxylic acid.

1 Claim, No Drawings

OPTICALLY ACTIVE PHOSPHINE OXIDE CARBOXYLIC ACID AND METHOD OF PRODUCING THE SAME

BACKGROUND OF THE INVENTION

1. Field of the Invention

The present invention relates to an optically active phosphine oxide carboxylic acid and the method of producing the same. The phosphine oxide having its asymmetric center at a phosphorus atom is a compound especially useful as a precursor of an optically active phosphine compound which may be used as a ligand of an asymmetric synthesis catalyst.

2. Description of the Prior Art

The oldest known method of producing an optically active phosphine oxide is by reacting an α-bromocamphor sulfonic acid to a methyl ethyl phenyl phosphine oxide, the produced salt being separated and crystallized, and then treated by ammonia to obtain an optically active phosphine oxide. (J. Meisenheimer, L. Lichtenstadt, Ber., 44, 356 (1911)).

The above-mentioned method utilizes the difference in the solubility of a diastereomer generated by the acidic of the camphor sulfonic acid and the basic of the phosphine oxide. However, since a camphor sulfonic acid (camphor) which is a natural product is used as the separating agent, there is a drawback that camphor with sufficient purity may not be obtained when isolating the same from natural products.

Therefore, another known method of obtaining an optically active phosphine oxide comprises the following steps. A thionyl chloride and an optically active 1-menthol is reacted under the existence of a triethylamine to a phosphinic acid of a different alkyl group such as a methylphenyl phosphinic acid, so as to obtain a diastereomer salt of a menthyl methyl phenyl phosphinate. The salt is separated and crystallized, and treated by base to obtain an optically active menthyl methyl phenyl phosphinate. Moreover, an optically active phosphine oxide is also known to be obtained by reacting a Grignard reagent. (Homogeneous Catalysis II, Adv. Chem. Ser., No. 132,274 (1974)).

This method utilizes an equivalent stoichiometric amount of 1-menthol which is an asymmetric source, and introduces the same by a covalent bond to a phosphinic acid which is a reaction substrate. However, this method uses a large amount of expensive asymmetric source, and moreover, the portion of the asymmetric source introduced by the covalent bond after the reaction must be removed and collected by a chemical process of some kind. Therefore, such asymmetric reaction may be used for a compound having high additional values such as a prostaglandin, but is not practical as a general industrial process.

SUMMARY OF THE INVENTION

Upon careful study of the conventional problems, the present inventors discovered and completed a most reasonable method to obtain an optically active compound having various compositions, which is an optical resolution method utilizing the solubility of the diastereomer salt. The present invention utilizes an optically active amine which may be easily obtained and is not expensive, such as 1-phenylethylamine, and uses a phosphine oxide carboxylic acid of a racemic modification, in order to obtain an optically active phosphine oxide carboxylic acid easily.

The optically active phosphine oxide carboxylic acid according to the present invention is a novel compound, and the method of producing such compound is also novel.

The object of the present invention is to utilize a reagant for optical resolution which may be easily obtained and is not so expensive, in order to provide a novel optically active phosphine oxide and the method of producing the same through a simple procedure.

The present invention provides the following:

An optically active phosphine oxide carboxylic acid shown by the following general formula (1):

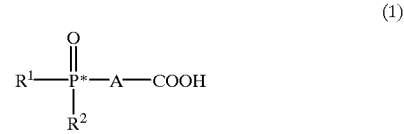

(1)

(in the formula, $R^1$ and $R^2$ represent a linear or branched alkyl group, hydroxyalkyl group or aminoalkyl group with 1–18 carbons, or a substituted or non-substituted phenyl group, wherein $R^1$ and $R^2$ differ from one another, and A represents a linear or branched alkylene group).

Moreover, the present invention provides the following:

A method of producing an optically active phosphine oxide carboxylic acid, wherein an optically active 1-phenylethylamine is reacted to a phosphine oxide carboxylic acid of a racemic modification shown by the following general formula (2):

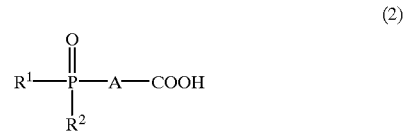

(2)

(in the formula, $R^1$, $R^2$ and A represent what are defined above), and a produced diastereomeric salt is separated using the difference in solubility against a solvent which is subsequently decomposed by acid, so as to free and separate an optically active phosphine oxide carboxylic acid.

PREFERRED EMBODIMENT OF THE INVENTION

The present invention will now be explained in detail.
(Optically Active Phosphine Oxide Carboxylic Acid)

The optically active phosphine oxide carboxylic acid of the present invention is shown by a general formula (1). In the formula, A represents a linear or branched alkylene group such as a methylene group, ethylene group, trimethylene group, tetramethylene group and the like, and preferably represents a linear alkylene group with 1–4 carbons. Moreover, $R^1$ and $R^2$ are not especially limited, but represent a linear or branched alkyl group, hydroxyalkyl group or aminoalkyl group with 1–18 carbons, or a substituted or non-substituted phenyl group, wherein $R^1$ and $R^2$ are different optically active substances with their asymmetric center placed on a phosphorus atom.

Compounds such as (−)-(S)-[(carboxymethyl) (1,1,3,3-tetramethylbutyl) methyl] phosphine oxide, (+)-(R)-[(carboxymethyl) (1,1,3,3-tetramethylbutyl) methyl] phosphine oxide, (−)-(S)-[(2-carboxyethyl) (1,1,3,3-tetramethylbutyl) methyl] phosphine oxide, (+)-(R)-[(2-carboxyethyl) (1,1,3,3-tetramethylbutyl) methyl] phosphine oxide, (−)-(S)-[(carboxymethyl) (1,1,3,3-tetramethylbutyl) ethyl] phosphine oxide, (+)-(R)-[(carboxymethyl) (1,1,3,3-tetramethylbutyl) ethyl] phosphine oxide, (−)-(S)-[(carboxymethyl) (1,1,3,3-tetramethylbutyl) (1,1,-dimethylethyl)] phosphine oxide, (+)-(R)-[(carboxymethyl) (1,1,3,3-tetramethylbutyl) (1,1,-dimethylethyl)] phosphine oxide, (−)-(S)-[(carboxymethyl) (o-methoxyphenyl) phenyl] phosphine oxide, (+)-(R)-[(carboxymethyl) (o-methoxyphenyl) phenyl] phosphine oxide, (−)-(S)-[(carboxymethyl) (o-ethylphenyl) phenyl] phosphine oxide, (+)-(R)-[(carboxymethyl) (o-ethylphenyl) phenyl] phosphine oxide, and so on may be used as the actual compound of the present invention.

Producing Method According to the Present Invention (Starting Material)

The starting material used in the producing method according to the present invention is shown by a general formula (2):

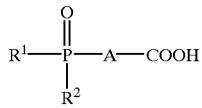
(2)

As shown in the formula (wherein the definitions of $R^1$, $R^2$ and A are the same as those explained above), the starting material is a phosphine oxide carboxylic acid of a racemic modification, and the letter A in the formula represents a linear or branched alkylene group such as a methylene group, ethylene group, trimethylene group, tetramethylene group and the like, and preferably represents a linear alkylene group with 1–4 carbons. Moreover, $R^1$ and $R^2$ are not especially limited, but represent a linear or branched alkyl group, hydroxyalkyl group or aminoalkyl group with 1–18 carbons, or a substituted or non-substituted phenyl group, and $R^1$ and $R^2$ are not the same.

(Solvent)

The solvent to be used in the present invention may be acetone, methyl ethyl ketone or MIBK and the like of the ketone class, and especially, acetone or methyl ethyl ketone is preferable. The amount of the solvent to be used differs according to the solubility, but generally, the appropriate amount should be five to ten times the amount (weight ratio) of the solute.

(Optical Resolution Method)

The amount of use of the optically active 1-phenylethylamine which acts as the reagent for optical resolution should range in a ratio of 0. 7–1. 0 mol against a phosphine oxide carboxylic acid of a racemic modification. The reaction is a neutralization reaction, so there is no need for a special reaction condition. The mixing method may also be optional, and it may be mixed directly into the solvent, or each solution may be mixed together. A homogeneous solution is obtained at a reacting temperature of either the room temperature or a heated temperature below the boiling point of the solvent, and the solution is then deposited statically for the deposition of a refractory diastereomeric salt. The deposition temperature may be either the room temperature or a temperature cooled by a cooler or a refrigerator. Normally at this state, inoculation of the seed crystal of the salt to be deposited is performed.

The deposited salt is separated from the solvent by filtration or centrifugal separation, and recrystallization and purification may be performed thereto according to need. The obtained salt is processed by strong acid such as hydrochloric acid or sulfuric acid so as to decompose the salt, and by performing extraction by a solvent not mixed with water capable of solving phosphine oxide carboxylic acid, an optically active phosphine oxide carboxylic acid may be obtained. Further, recrystallization and purification may be performed thereto according to need.

The optically active phosphine oxide carboxylic acid obtained by the above method is a novel compound, which is especially useful as a precursor of an optically active phosphine compound which may be utilized as a ligand of an asymmetric synthesis catalyst.

The optically active 1-phenylethylamine used in the optical resolution may be easily retrieved by reacting the aqueous solution after the solvent extraction of phosphine oxide carboxylic acid to a strong bases such as sodium hydroxide or potassium hydroxide and the like, and performing a solvent extraction or vacuum distillation thereto. The retrieved 1-phenylethylamine may be reused.

Embodiment 1

(Synthesis of Racemic Modification)

A stainless steel autoclave with an approximately one-liter reaction container and including an agitator is used. After performing a nitrogen substitution to the interior of the autoclave, 300 ml of n-hexane, 122.2 g (1.0 mol) of isobutylene dimer (mixture including 75% of 2,4,4-trimethyl-1-penten and 22% of 2,4,4-trimethyl-2-penten), and 34.0 g (1.0 mol) of phosphine are added thereto under room temperature. The reaction temperature is then raised to 80° C., and 96.1 g (1.0 mol) of methanesulfonic acid is further added by an injection pump taking approximately three hours of time. The pressure inside the autoclave is decreased from 12.5 atm to 4.5 atm. Further, aging is performed for four hours maintaining a temperature of 80° C. After the reaction, the temperature is cooled to room temperature, unreacted phosphine is discharged, and sufficient nitrogen substitution is performed to the interior of the system. The reaction product is taken out from the autoclave, and after statically depositing the product for twenty-four hours, separation is performed and the methanesulfonic acid of the lower layer is removed. By performing a vacuum distillation of the n-hexane layer, a water-clear liquid weighing 98.3 g is obtained. The liquid is a 1,1,3,3-tetramethylbutyl phosphine having a boiling point of 79–80° C. (62 mmHg).

The analysis result by an NMR of the liquid is as follows: $^1$H-NMR (ppm, CDCl$_3$); 1.02 (s, 9H, CH$_3$), 1.32 (d, 6H, JPCCH=10.8 Hz, CH$_3$), 1.51 (d, 2H, CH$_2$, JPCCH=13.2 Hz), 2.92 (d, 2H, P-H, JPH=190.8 Hz); GC-MASS (EI); m/z=146 [M+]; FT-IR (KBr, cm$^{-1}$); 2959, 2880, 2275, 1465, 1360, 1065.

A four-mouth flask having a capacity of 1000 ml and equipped with an agitator, a thermometer, a dropping funnel and a condenser is sufficiently nitrogen-substituted, and 73.1 g (0.5 mol) of 1,1,3,3-tetramethylbutyl phosphine and 212.9 g (1.5 mol) of methyl iodide are placed thereto under room temperature. When the temperature is raised to a breakthrough temperature, the liquid turns white and crystal is deposited, which is then heated so that it becomes difficult to agitate. Then under reduced pressure, excessive ethyl iodide is removed, 200 ml of high purity water and 200 ml of n-hexane is added thereto, and a caustic soda solution of 1.1 times mol is added. After cooling, the liquid is separated under nitrogen atmosphere, and the hexane layer is concentrated, and vacuum distillation is performed thereto, so as to obtain a water-clear liquid weighing 63.9 g. This is a (1,1,3,3-tetramethylbutyl) methyl phosphine having a boiling point of 63–66° C. (16 mmHg).

The analysis result by an NMR of the substance is as follows: $^1$H-NMR (ppm, CDCl$_3$); 1.11 (s, 9H, CH$_3$), 1.65 (d, 6H, JPCCH=20.2 Hz, CH$_3$), 1.79 (d, 2H, CH$_2$, JPCCH=15.4 Hz), 2.16 (d, 3H, P-CH$_3$, JPCH=15.0 Hz), 7.56 (d, 1H, P-H, JPH=497.2 Hz); GC-MASS (EI); m/z=160 [M+]; FT-IR (KBr, cm$^{-1}$); 2965, 2280, 1470, 1364, 1296, 1236, 972.

A four-mouth flask with a capacity of 1000 ml and equipped with an agitator, a thermometer, a dropping funnel and a condenser is sufficiently nitrogen-substituted, and 48.0 g (0.3 mol) of (1,1,3,3-tetramethylbutyl) methyl phosphine and 150 ml of ethanol is placed thereto. Then, 100.2 g (0.9 mol) of brom ethyl acetate is dropped thereto, and it is aged for three hours under a break-through temperature, concentrated by an evaporator, and the solvent is removed therefrom. Further, 200 ml of high purity water is added thereto, and a sodium hydroxide solution of 2.2 times mol is dropped under room temperature. It is further aged for three hours under break-through temperature. Extraction is performed two times using dichloromethane, and the obtained organic layer is washed by a 0.1 N hydrochloric acid solution, and it is further washed by high purity water. The organic layer is dehydrated by sodium sulfate anhydride, statically deposited for twenty-four hours, filtered and then concentrated by an evaporator to obtain a white-colored solid body. By recrystallization and purification through acetone, 17.1 g of white-colored crystal having a boiling point of 99–100° C. is obtained. According to analysis results, this is a [(carboxymethyl) (1,1,3,3-tetramethylbutyl) methyl] phosphine oxide. $^1$H-NMR (ppm, CDCl$_3$); 1.06 (s, 9H, CH$_3$), 1.34 (d, 6H, JPCCH=17.9 Hz, CH$_3$), 1.52 (d, 2H, CH$_{21}$ JPCCH=8.8 Hz), 1.71 (d, 3H, P-CH$_3$, JPCH=12.3 Hz), 2.71 (dd, 1H, JPCH=9.2 Hz, Jgem=13.4 Hz, P-CH-), 3.00 (dd, 1H, J=14.3 Hz, Jgem=13.4 Hz, P-CH'-), 10.78 (s, 1H, COOH); FAB-MASS (Pos.); m/z=235 [M+H+]; FT-IR (KBr, cm$^{-1}$); 2955, 2872, 1714, 1270, 1158, 1103, 970, 896; UV-VIS (MeOH); εmax=40.5, λmax=217.6 nm.

(Optical Resolution)

In a flask having a capacity of 300 ml, 16.7 g (71.5 mmol) of the obtained [(carboxymethyl) (1,1,3,3-tetramethylbutyl) methyl] phosphine oxide and 200 ml of methyl ethyl ketone is placed, and 8.7 g (71.5 mmol) of (−)-(S)-1-phenylethylamine is added thereto. It dissolved completely while generating some heat. The solution is statically deposited for twenty-four hours under room temperature, thereby depositing crystal. The crystal is then filtered and vacuum dried, so as to obtain 20.5 g of white-colored crystal. The crystal has a boiling point of 121–123° C., and the angle of rotation is [α] 25D=−1.89 (c 1.212 CHCl$_3$). Subsequently, 220 ml of acetone is used for recrystallization, so as to obtain 3.7 g of white-colored crystal. A partial sample is freed by hydrochloric acid, and a phosphine oxide obtained by extraction through dichloromethane is analyzed. The phosphine oxide has a boiling point of 115–117° C., and an optical purity of o.p.=66.5% e.e. (HPLC). It is further recrystallized using 150 ml of acetone, and as a result, 2.6 g of white-colored crystal is obtained. This is freed by hydrochloric acid, and extracted by dichloromethane, so as to obtain 1.2 g of white-colored crystal. According to analysis, the substance is a (−)-(S)-[(carboxymethyl) (1,1, 3,3-tetramethylbutyl) methyl] phosphine oxide having a boiling point of 99–100° C., an optical purity of o.p.=98.6% e.e. (HPLC), and an angle of rotation of [α] 25D=−15.8 (c 1.040 CHCl$_3$).

The result of analysis of the substance by NMR is as follows: $^1$H-NMR (ppm, CDCl$_3$); 1.06 (s, 9H, CH$_3$), 1.34 (d, 6H, JPCCH=18.0 Hz, CH$_3$), 1.53 (d, 2H, CH$_2$, JPCCH=8.7 Hz), 1.69 (d, 3H, P-CH$_3$, JPCH=12.0 Hz), 2.71 (dd, 1H, JPCH=9.6 Hz, Jgem=13.2 Hz, P-CH-), 3.04 (dd, 1H, J=15.3 Hz, Jgem 13.2 Hz, P-CH'-), 11.32 (s, 1H, COOH); FAB-MASS (Pos.); m/z=235 [M+H+];

Embodiment 2

A filtration mother liquor after separating the (−)-(S)-[(carboxymethyl) (1,1,3,3-tetramethylbutyl) methyl] phosphine oxide from the [(carboxymethyl) (1,1,3,3-tetramethylbutyl) methyl] phosphine oxide of the racemic modification according to embodiment 1, which is a (+)-(R)-[(carboxymethyl) (1,1,3,3-tetramethylbutyl) methyl] phosphine oxide-rich (+)-(R)-[(carboxymethyl) (1,1,3,3-tetramethylbutyl) methyl] phosphine oxide/(−)-(S)-1-phenylethylamine salt, is statically deposited for twenty-four hours to deposit crystal.

The crystal is filtered, vacuum dried, and 2.6 g of white-colored crystal is obtained. A partial sample of the crystal is freed by hydrochloric acid, and a phosphine oxide carboxylic acid obtained by extracting the same by dichloromethane is analyzed. It had a boiling point of 117–118° C., and the optical purity is o.p.=55.6% e.e. (HPLC). Further, through recrystallization performed using 100 ml of acetone, 1.5 g of white-colored crystal is obtained. This is freed by hydrochloric acid, and extracted by dichloromethane, so as to obtain 1.5 g of white-colored crystal. According to analysis, the substance is a (+)-(R)-[(carboxymethyl) (1,1,3,3-tetramethylbutyl) methyl] phosphine oxide having a boiling point of 98–99 ° C., an optical purity of o.p.=93.7% e.e. (HPLC), and an angle of rotation of [α] 25D=+14.8 (c 1.284 CHCl$_3$).

The result of analysis of the substance by NMR is as follows: $^1$H-NMR (ppm, CDCl$_3$); 1.06 (s, 9H, CH$_3$), 1.35 (d, 6H, JPCCH=17.9 Hz, CH$_3$), 1.56 (d, 2H, CH$_2$, JPCCH=8.3 Hz), 1.67 (d, 3H, P-CH$_3$, JPCH=10.9 Hz), 2.84 (dd, 1H, JPCH=9.2 Hz, Jgem=13.4 Hz, P-CH-), 3.02 (dd, 1H, J=14.3 Hz, Jgem=13.4 Hz, P-CH'-), 10.36 (s, 1H, COOH); FAB-MASS (Pos.); m/z=235 [M+H+].

Embodiment 3

(Synthesis of Racemic Modification)

A four-mouth flask with a capacity of 300 ml and equipped with an agitator, a thermometer, a dropping funnel and a condenser is sufficiently nitrogen-substituted, and 16.0 g (0.1 mol) of (1,1,3,3-tetramethylbutyl) methyl phosphine obtained by embodiment 1 and 15.6 g (0.15 mol) of concentrated hydrochloric acid is placed thereto. Then, while cooling and maintaining the temperature to 20–25 ° C., 7.2 g (0.1 mol) of acrylic acid is dropped. Thereafter, it is aged for two hours under a temperature of 40 ° C., concentrated by an evaporator, and excessive hydrochloric acid is removed therefrom. Further, 100 ml of high purity water is added thereto, and the temperature is raised to 80 ° C., and 10.7 g (0.11 mol) of 35% hydrogen peroxide water is gradually dropped thereto while maintaining a fixed temperature. It is further aged under the same temperature for three hours. A viscous body obtained by concentration is treated by acetone for recrystallization and purification, and 15.8 g of white-colored crystal having a boiling point of 100–103° C. is obtained. According to the result of analysis, this is a [(2-carboxyethyl) (1,1,3,3-tetramethylbutyl) methyl] phosphine oxide.

The result of analysis of the substance by NMR is as follows: $^1$H-NMR (ppm, CDCl$_3$); 1.06 (s, 9H, CH$_3$), 1.35 (d, 6H, JPCCH=17.6 Hz, CH$_3$), 1.50 (d, 2H, CH$_2$I JPCCH=8.6 Hz), 1.59 (d, 3H, P-CH$_3$, JPCH=11.7 Hz), 1.92–2.27 (m, 2H, P-CH$_2$-), 2.57–2.80 (m, 2H, —CH$_2$—COO), 11.81 (s, 1H, COOH); FAB-MASS (Pos.); m/z=249 [M+H+]; FT-IR (KBr, cm$^{-1}$); 2953, 2918, 1735, 1422, 1233, 1171, 1112, 964, 903; UV-VIS (MeOH); εmax=140.1, λmax=218.1 nm.

(Optical Resolution)

In a flask having a capacity of 50 ml, 3.03 g (12.2 mmol) of the obtained [(2-carboxyethyl) (1,1,3,3-tetramethylbutyl) methyl] phosphine oxide and 4.5 ml of acetone is placed, and 1.48 g (12.2 mmol) of (+)-(R)-1-phenylethylamine is added thereto. It dissolved completely while generating some heat. The solution is statically deposited for twenty-four hours under 0° C., thereby depositing crystal. The crystal is then filtered and vacuum dried, so as to obtain 0.83 g of white-colored crystal. The crystal has a boiling point of 135–138° C., and an angle of rotation of [α] 25D=+3.42 (c 1.072 CH₃OH). This is freed by hydrochloric acid, and extracted by dichloromethane, so as to obtain 0.11 g of white-colored crystal. According to analysis, the substance is a (−)-(S)-[(2-carboxyethyl) (1,1,3,3-tetramethylbutyl) methyl] phosphine oxide having a boiling point of 145–146° C., and an angle of rotation of [α] 25D=−8.17 (c 1.040 CH₃OH).

The result of analysis of the substance by NMR is as follows: ¹H-NMR (ppm, CDCl₃); 1.06 (S, 9H, CH₃), 1.33 (d, 6H, JPCCH=17.0 Hz, CH₃), 1.50 (d, 2H, CH₂, JPCCH= 8.4 Hz), 1.49 (d, 3H, P-CH₃, JPCH=11.7 Hz), 1.78–2.16 (m, 2H, P-CH₂-), 2.46–2.71 (m, 2H, —CH₂—COO), 10.34 (s, 1H, COOH); FAB-MASS (Pos.); m/z=249 [M+H+].

Embodiment 4

In a flask having a capacity of 50 ml, 3.05 g (12.3 mmol) of the [(2-carboxyethyl) (1,1,3,3-tetramethylbutyl) methyl] phosphine oxide obtained by embodiment 2 and 4.5 ml of acetone is placed, and 1.48 g (12.2 mmol) of (−)-S-1-phenylethylamine is added thereto, which is then statically deposited for twenty-four hours under 0° C., so as to deposit crystal. The crystal is then filtered and vacuum dried, so as to obtain 0.32 g of white-colored crystal. The crystal has a boiling point of 126–131° C. This is freed by hydrochloric acid, and extracted by dichloromethane, so as to obtain 0.18 g of white-colored crystal. According to analysis, the substance is a (+)-(R)-f(2-carboxyethyl) (1,1,3,3-tetramethylbutyl) methyl) phosphine oxide having a boiling point of 144–146° C., and an angle of rotation of [α] 25D=+6.30 (c 0.238 CH₃OH).

The result of analysis of the substance by NMR is as follows: ¹H-NMR (ppm, CDCl₃); 1.06 (s, 9H, CH₃), 1.33 (d, 6H, JPCCH=17.0 Hz, CH₃), 1.50 (d, 2H, CH₂, JPCCH=8.4 Hz), 1.49 (d, 3H, P-CH₃, JPCH=11.7 Hz), 1.83–2.22 (m, 2H, P-CH₂-), 2.53–2.76 (m, 2H, —CH₂—COO), 10.72 (s, 1H, COOH); FAB-MASS (Pos.); m/z=249 [M+H+].

The present invention composed as above utilizes an optically active amine such as 1-phenylethylamine which is easy to get and not so expensive, in order to easily obtain an optically active phosphine oxide carboxylic acid from a phosphine oxide carboxylic acid of a racemic mixture. The optically active phosphine oxide carboxylic acid according to the present invention is a novel compound, and said compound is especially useful as a precursor of an optically active phosphine compound which may be utilized as a ligand of an asymmetric synthesis catalyst.

We claim:

1. A method of producing an optically active phosphine oxide carboxylic acid, wherein an optically active 1-phenylethylamine is reacted to a phosphine oxide carboxylic acid of a racemic modification shown by the following general formula (2):

(2)

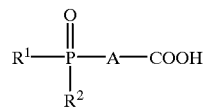

* * * * *